(12) United States Patent
Jo et al.

(10) Patent No.: US 8,231,610 B2
(45) Date of Patent: Jul. 31, 2012

(54) ROBOTIC SURGICAL SYSTEM FOR LAPAROSCOPIC SURGERY

(75) Inventors: Yung-Ho Jo, Gyeonggi-do (KR); Dong-Jun Kim, Gyeonggi-do (KR); Jaesoon Choi, Gyeonggi-do (KR); Jae-Gahb Park, Seoul (KR); Young-Woo Kim, Seoul (KR); Sang-Jae Park, Gyeonggi-do (KR)

(73) Assignee: National Cancer Center, Gyeonggi-Do (KR)

( * ) Notice: Subject to any disclaimer, the term of this patent is extended or adjusted under 35 U.S.C. 154(b) by 1649 days.

(21) Appl. No.: 11/515,738

(22) Filed: Sep. 6, 2006

(65) Prior Publication Data

US 2008/0058776 A1     Mar. 6, 2008

(51) Int. Cl.
*A61B 19/00*     (2006.01)

(52) U.S. Cl. .................. 606/1; 606/2; 606/52; 606/130; 606/157; 606/170; 606/174; 606/206; 606/211; 600/429

(58) Field of Classification Search ............ 606/1, 41–52
See application file for complete search history.

(56) References Cited

U.S. PATENT DOCUMENTS 6,312,435 B1 * 11/2001 Wallace et al. ............... 606/130
6,394,998 B1 *  5/2002 Wallace et al. ............... 606/1

* cited by examiner

*Primary Examiner* — Aaron Roane
(74) *Attorney, Agent, or Firm* — Bacon & Thomas, PLLC

(57) ABSTRACT

A robotic surgical system includes a master manipulator, slave robotic units having a surgical instrument for performing a Minimal Invasive Surgery (MIS), and a control system for electrically associating the master manipulator with the slave robotic units. The slave robotic unit includes the driving mechanisms which are more compact than those of the conventional MIS system. In use, the existing surgical instruments used in the conventional MIS procedure can be applied to the slave robotic unit. Moreover, by using the pivotal mechanism of the driving mechanisms, a pivot point of the surgical instrument is allowed to be shifted with respect to an incision of a patient. So, the patient's tissues surrounding the surgical instrument are not excessively affected by the surgical instrument during the procedure.

20 Claims, 14 Drawing Sheets

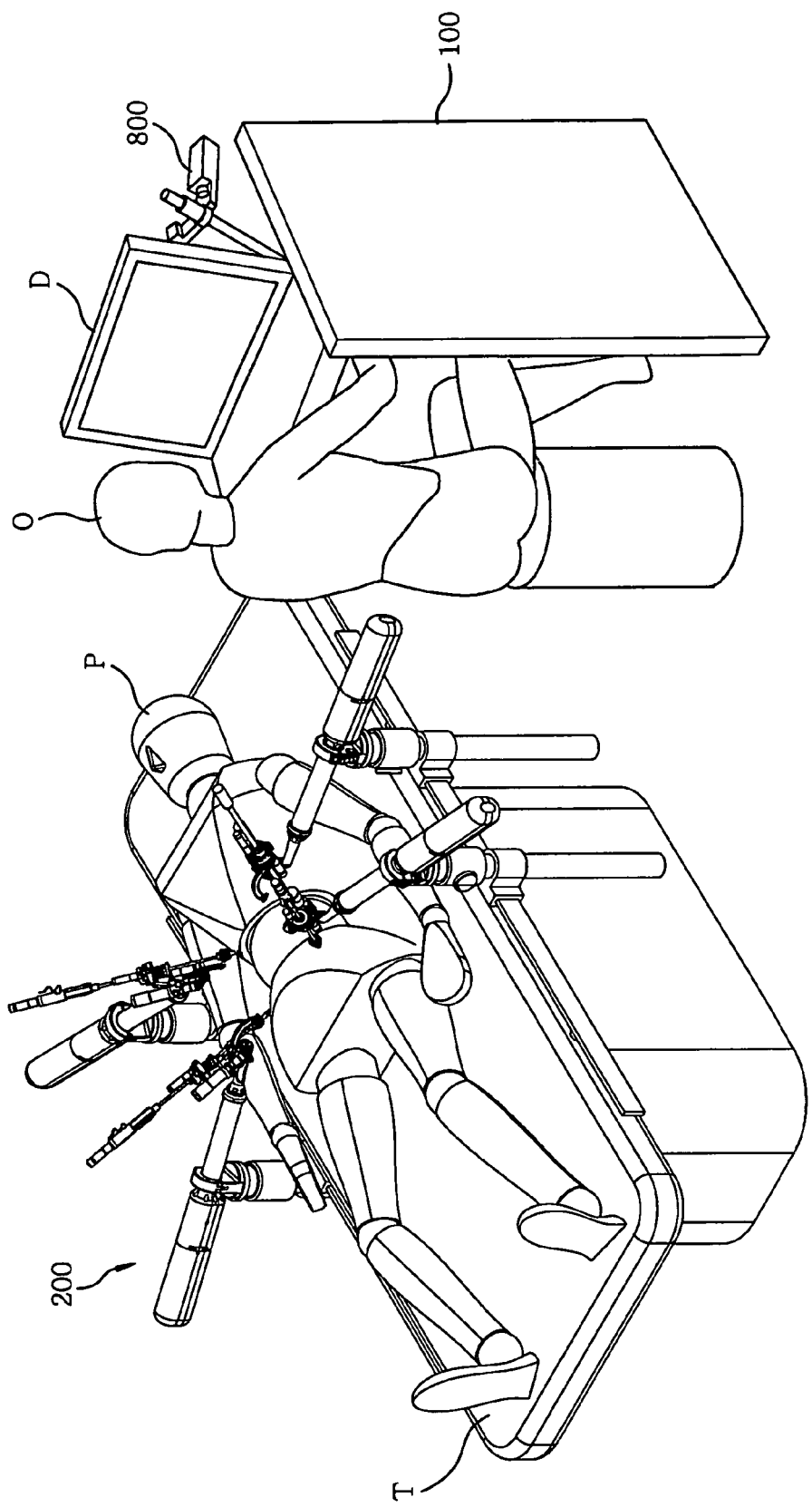

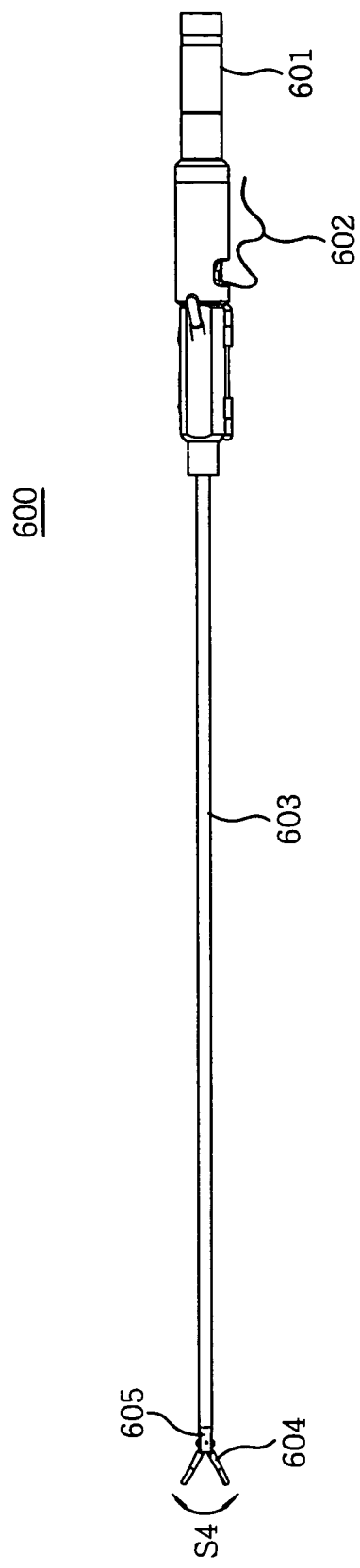

ROBOTIC SURGICAL SYSTEM FOR LAPAROSCOPIC SURGERY

FIELD OF THE INVENTION

The present invention relates to a robotic surgical system; and, more particularly, to a robotic surgical system having a plurality of compact slave robotic arms capable of performing laparoscopic surgery in minimal invasive manner.

BACKGROUND OF THE INVENTION

Generally, there have been attempts to perform a minimally invasive surgical (MIS) procedure. Such MIS techniques are aimed at reducing the amount of extraneous tissue that is damaged during diagnostic or surgical procedures, thereby reducing patient recovery time, discomfort, and deleterious side effects. The most common form of such procedures is laparoscopy, which is used for minimally invasive inspection and surgery inside the abdominal cavity. To perform such MIS procedures, a surgeon needs special instruments. The surgeon passes these instruments through a small incision of an abdominal wall to a surgical site and manipulates them from outside the abdominal wall by sliding them in and out through the abdominal wall, rotating and pivoting them against the abdominal wall. However, it has been found that a high level of dexterity is required to accurately control such instruments. And, the surgeon has no flexibility of tool replacement. Additionally, he or she experiences difficulty in approaching the surgical site through the incision. The length and construction of many instruments reduces the surgeon's ability to feel forces exerted by the surgical site on the instruments. Further, human hands typically have at least a minimal amount of tremor. The tremor further increases the difficulty of performing minimally invasive surgical procedures. So, only a relatively small number of surgeries have been performed due to limitations in required instruments, techniques and the surgical training.

Therefore, minimally invasive surgical robotic systems have been currently developed to increase a surgeon's dexterity when working within an internal surgical site as well as to allow a surgeon to operate on a patient from a remote location while monitoring a procedure by means of, e.g., a viewer which displays a three dimensional image of the surgical site via a camera. By means of the robotic systems, the surgeon can manipulate surgical instrument movements without directly holding and moving the instruments by hand. In such robotic systems, the surgical instruments can be precisely operated and be remotely controlled in a minimally invasive manner.

A robotic surgery is getting increasing attention with the wider application of the laparoscopic surgery. Actually, surgeons can do more efficient surgery with the enhanced dexterity and intelligent assistance provided by the robotic system.

Conventional robotic surgical systems are disclosed in e.g., U.S. Pat. No. 6,102,850 entitled "Medical Robotic System", and U.S. Pat. No. 6,364,888 entitled "Alignment of Master and Slave in a Minimally Invasive Surgical Apparatus". However, up to the present, the currently commercially available robotic surgical systems have drawbacks for abdominal surgery such as a huge system with bulky robotic arms, expensive cost, and so forth. Such a robotic system requires a large installation space and can not fully ensure an accurate surgical procedure.

SUMMARY OF THE INVENTION

It is, therefore, an object of the present invention to provide a robotic surgical system provided with a pivotal mechanism for adjusting a pivot point of a surgical instrument.

In accordance with the present invention, there is provided a robotic surgical system including:

a master manipulator installed at a control station to be manipulated by an operator; slave robotic units for performing a surgical procedure on a patient; a control system for electrically associating the master manipulator with the slave robotic units to allow each slave robotic unit to be remotely controlled by the associated master manipulator; and a display for viewing the surgical procedure conducted by the slave robotic units.

Each slave robotic unit includes:

a surgical instrument being inserted to a surgical site of the patient; a yaw driving mechanism for moving the surgical instrument in a yaw direction; a pitch driving mechanism for moving the surgical instrument in a pitch direction; a linear driving mechanism for linearly moving the surgical instrument; a rotational driving mechanism for rotating the surgical instrument about its longitudinal axis; an end tip driving mechanism for incising, sewing or cutting the surgical site; and a pivotal mechanism for allowing the surgical instrument to be freely pivoted.

Preferably, the pivotal mechanism includes: a lower part engaged with the pitch driving mechanism; a middle part pivotally connected to the lower part; and an upper part pivotally connected to the middle part, the upper part being fixed to the linear driving mechanism.

Preferably, the pivot movements of the middle part and the upper part are orthogonal to each other.

In accordance with the robotic surgical system of the present invention, the driving mechanisms are more compact than those of the conventional system. Furthermore, the existing surgical instruments used in the conventional MIS procedure can be applied to the robotic surgical system of the present invention. Moreover, the pivotal mechanism allows the pivot point of the surgical instrument to be shifted with respect to the incision, the patient's tissues surrounding the surgical instrument are not excessively affected by the surgical instrument during the procedure.

BRIEF DESCRIPTION OF THE DRAWINGS

The above and other objects and features of the present invention will become apparent from the following description, given in conjunction with the accompanying drawings, in which:

FIG. 1 is a perspective view of a robotic surgical system in accordance with a preferred embodiment of the present invention;

FIG. 6 is a side view of a surgical instrument of the slave robotic arm in accordance with the present invention;

DETAILED DESCRIPTION OF THE PREFERRED EMBODIMENTS

Hereinafter, a robotic surgical system in accordance with a preferred embodiment of the present invention will be described in detail with reference to the accompanying drawings.

Referring to FIG. 1, the robotic surgical system includes a plurality of slave robotic units 200 for performing a surgery on a patient P lying on an operation table T; and master manipulators 800, which are installed in a control station 100, for allowing an operator O to remotely control the slave robotic units 200. The control station 100 includes a control system (not shown) for converting movements of the master manipulator 800 into electrical signals; and a display D for allowing the operator O to see surgical procedures conducted by the slave robotic units 200. At least one of the slave robotic units 200 has an endoscope (not shown) for allowing the operator O to view a surgical site through the display D while doing an operation.

Figure 2A:
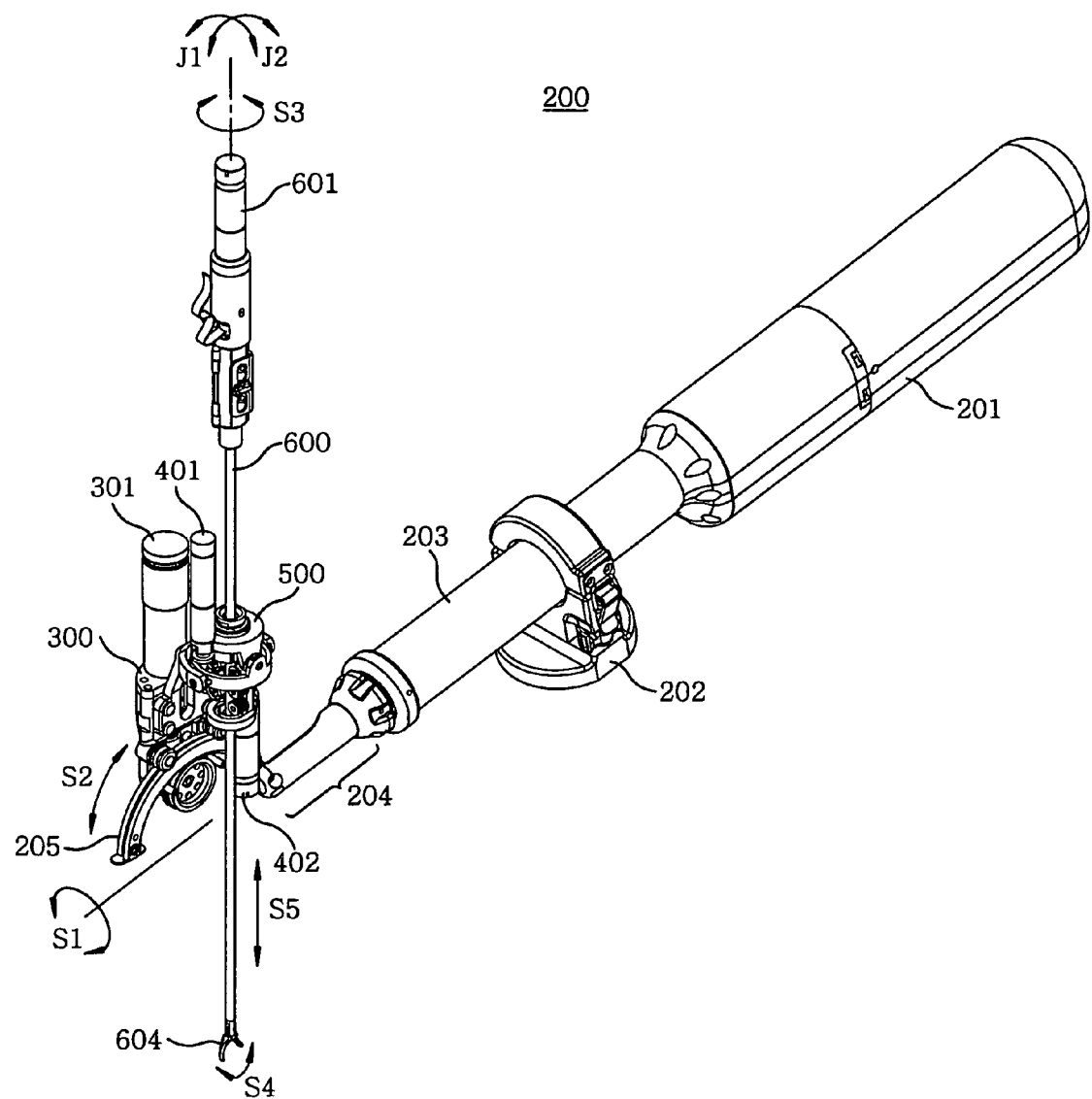
FIG. 2A is a perspective view of one of slave robotic arms of the robotic surgical system shown in FIG. 1.
Figure 2B:
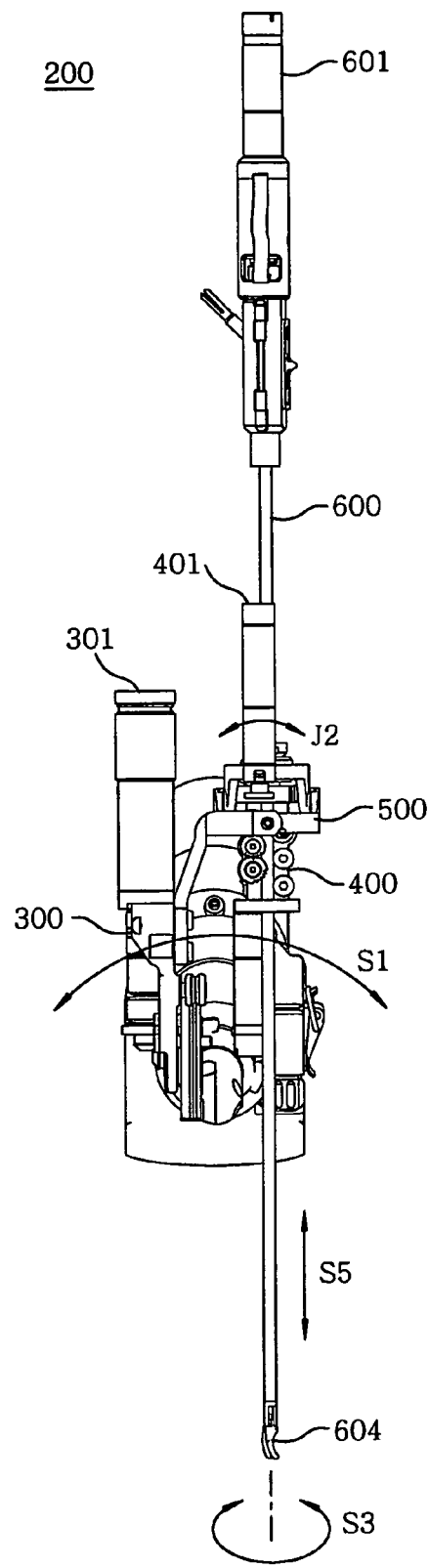
FIGS. 2B and 2C are a front view and a side view of the slave robotic arm shown in FIG. 2A, respectively.
Figure 2C:
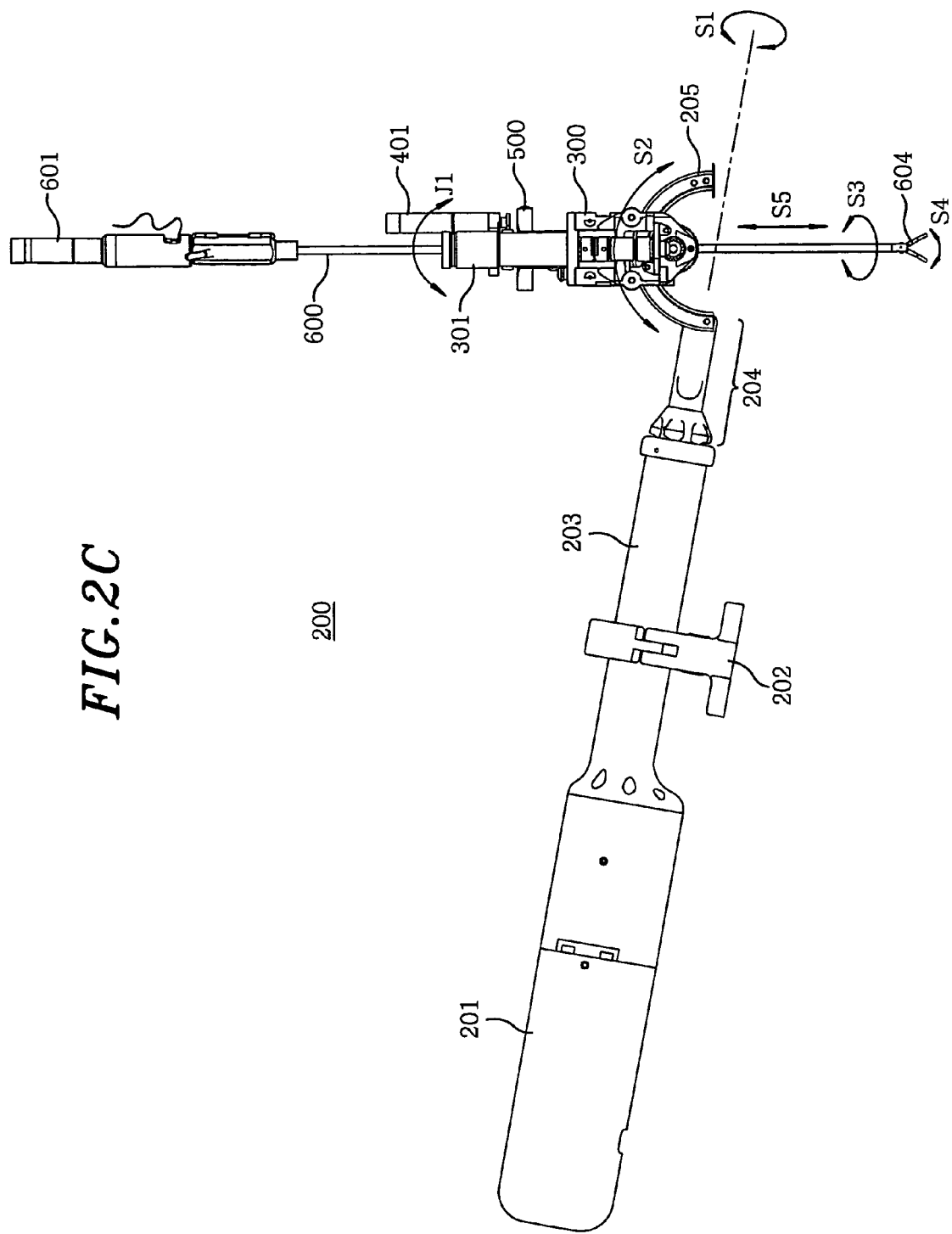

Referring to FIGS. 2A to 2C, the slave robotic unit 200 includes a wrist 204, a semicircular rack gear guide 205, a carriage 300, a linear guide 400, a pivotal mechanism 500 and a surgical instrument 600. The surgical instrument 600 is mounted on the slave robotic unit 200 and can reach the surgical site (not shown) through an incision (not shown). The slave robotic unit 200 further includes forearms 201, 203 and a holder 202. As shown in FIG. 1, the slave robotic unit 200 is fixedly mounted on the operation table T by using a holder 202.

The wrist 204 is pivotally coupled to a shaft (not shown) in the forearm 203 and is rotated clockwise or counterclockwise in a yaw direction as indicated by the arrows S1 by a motor (not shown) in the forearm 201. The shaft is outwardly protruded and engaged to one end of the wrist 204. Further, the semicircular rack gear guide 205 is fixedly coupled to the other end of the wrist 204.

Figure 3:
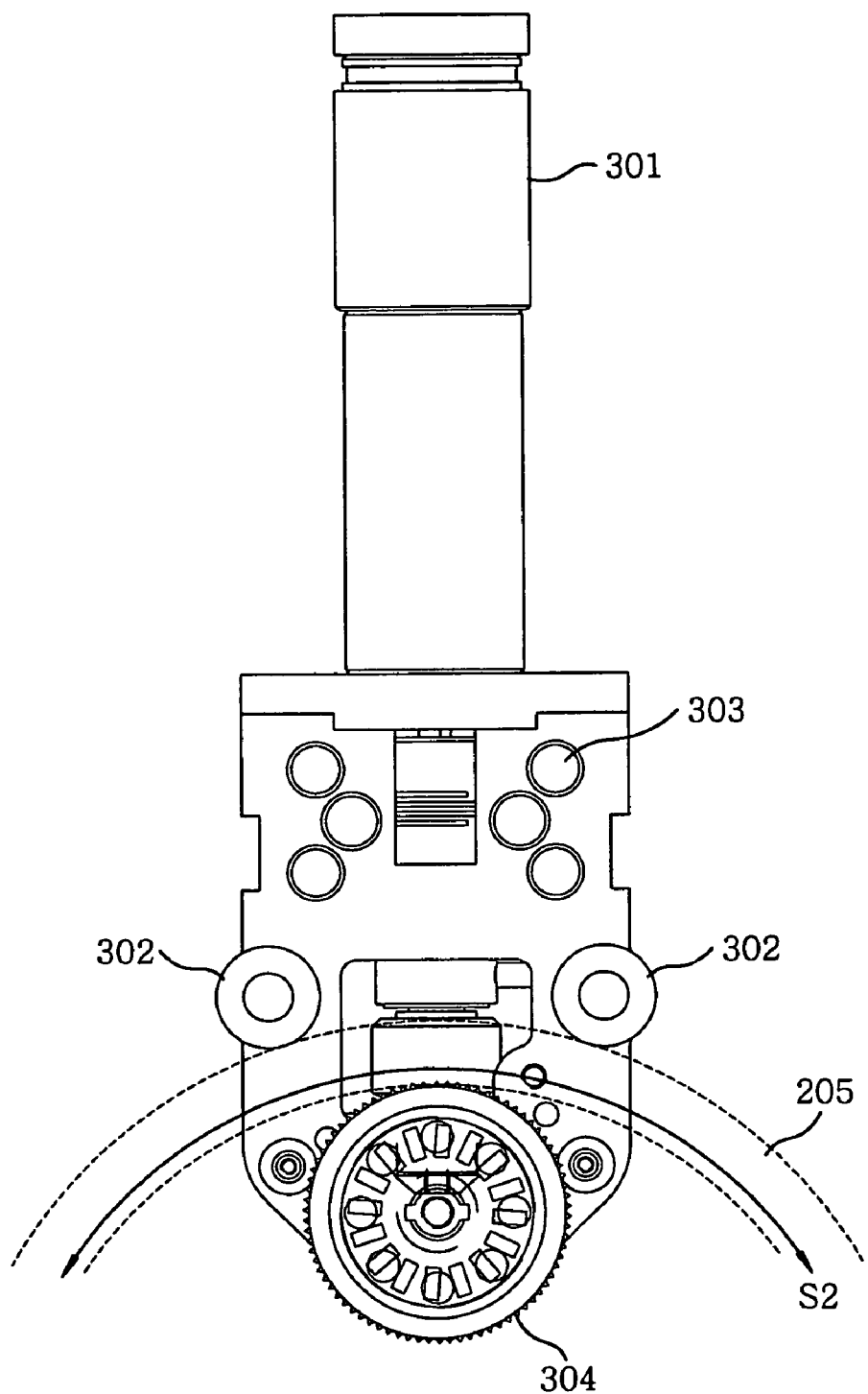
FIG. 3 is a front view of a carriage of the slave robotic arm in accordance with the present invention.

The carriage 300 is movably mounted on the semicircular rack gear guide 205. Referring to FIG. 3, the carriage 300 includes a motor 301, a pair of guide rollers 302, connectors 303 and a pinion gear 304 being rotated by the motor 301. The semicircular rack gear guide 205 (indicated by the dashed lines in FIG. 3) is provided between the guide rollers 302 and the pinion gear 304. Accordingly, the carriage 300 can be moved along the semicircular rack gear guide 205 in a pitch direction as indicated by the arrows S2. So, the carriage 300 can be moved in two degrees of freedom along the arrows S1 and S2. Additionally, the carriage 300 is coupled via the connectors 303 to the pivotal mechanism 500 to be described later.

Figure 4A:
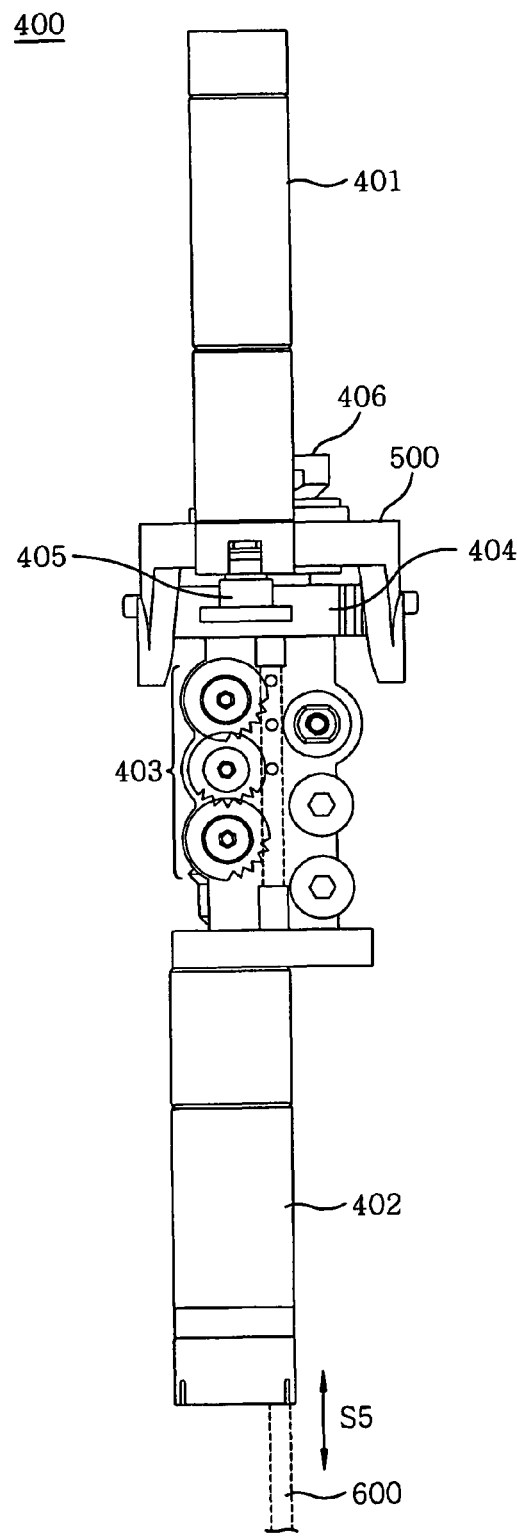
FIGS. 4A and 4B are a front view and a side view of a linear guide of the slave robotic arm in accordance with the present invention, respectively.
Figure 4B:
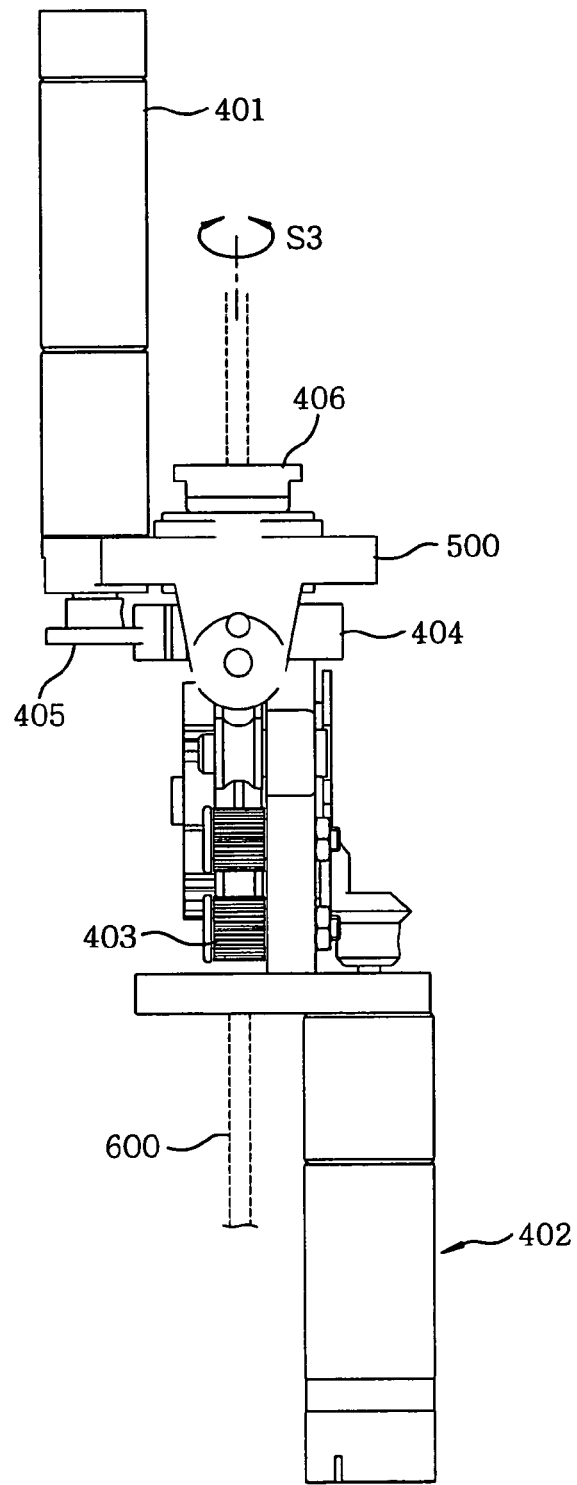

FIGS. 4A and 4B show the linear guide 400 including motors 401, 402, rollers 403, a fastener 406, and gears 404, 405. The upper motor 401 allows the surgical instrument 600 (shown by the dashed lines in FIGS. 4A and 4B) to rotate as indicated by the arrows S3, and the lower motor 402 allows the surgical instrument 600 to move up and down linearly as indicated by the arrows S5. The rotational movement S3 is controlled by the gears 404 and 405 which are driven by the upper motor 401, and the linear movement S5 is controlled by the rollers 403 which are driven by the lower motor 402. The surgical instrument 600 is positioned between the rollers 403 to be moved linearly by rotations of the rollers 403. Additionally, the pivotal mechanism 500 is fixedly mounted on the linear guide 400 by using the fastener 406.

As described above, the slave robotic unit 200 is provided with the yaw driving mechanism, the pitch driving mechanism, the linear driving mechanism and the rotational driving mechanism. The slave robotic unit 200 is further provided with the end tip driving mechanism and the pivotal mechanism 500 as will be described later.

The yaw driving mechanism serves to move the surgical instrument 600 in the yaw direction S1. The yaw driving mechanism includes the forearms 201 and 203; the motor (not shown) installed in the forearm 201; the shaft (not shown) rotated by the motor; and the wrist 204 coupled to the shaft. The wrist 204 is moved in the yaw direction S1 by the shaft.

The pitch driving mechanism serves to move the surgical instrument 600 in the pitch direction S2. The pitch driving mechanism includes the semicircular rack gear guide 205 coupled to the wrist 204; the carriage 300 movably mounted on the semicircular rack gear guide 205; the motor 301, the pinion gear 304 and the guide rollers 302. The carriage 300 is moved along the semicircular rack gear guide 205 in the pitch direction S2. Further, the carriage 300 is also rotated in the yaw direction S1 about an axis of the wrist 204 together with the semicircular rack gear guide 205 rotated by the yaw driving mechanism.

The linear driving mechanism serves to move the surgical instrument 600 linearly through the incision as indicated by the arrows S5. The linear driving mechanism includes the linear guide 400, the lower motor 402 and the rollers 403 provided in the linear guide 400. The rollers 403 are driven by the lower motor 402. The surgical instrument 600 is inserted between the rollers 403 so as to be linearly moved by the rollers 403.

The rotational driving mechanism includes the upper motor 401 and the gears 404, 405 of the linear guide 400. The gear 404 is driven by the rotation of the gear 405, to thereby rotate the surgical instrument 600 as indicated by the arrows S3.

Figure 5A:
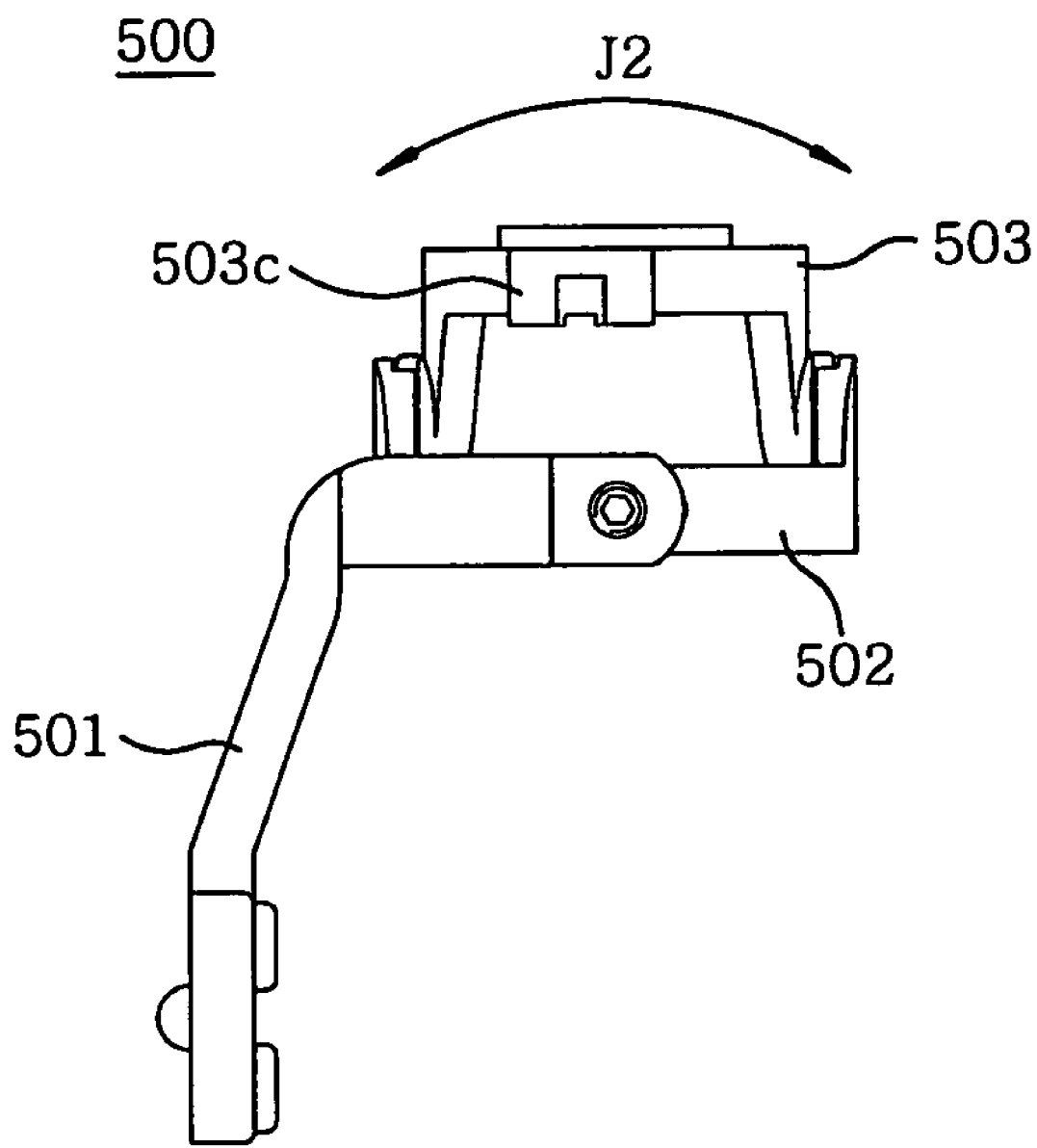
FIG. 5A is a side view of a pivotal mechanism in accordance with the present invention.
Figure 5B:
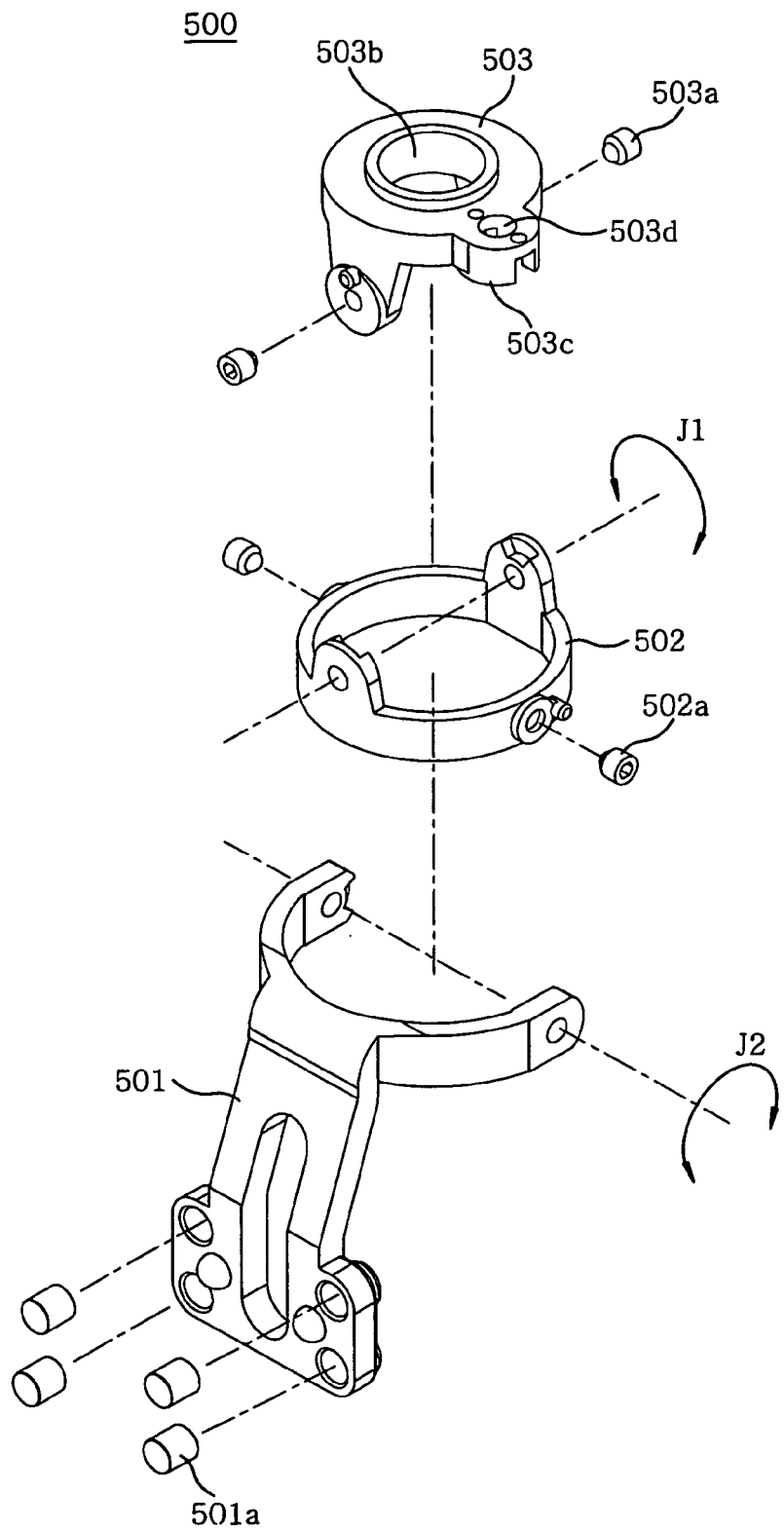
FIG. 5B is an exploded perspective view of the pivotal mechanism shown in FIG. 5A.
Figure 5C:
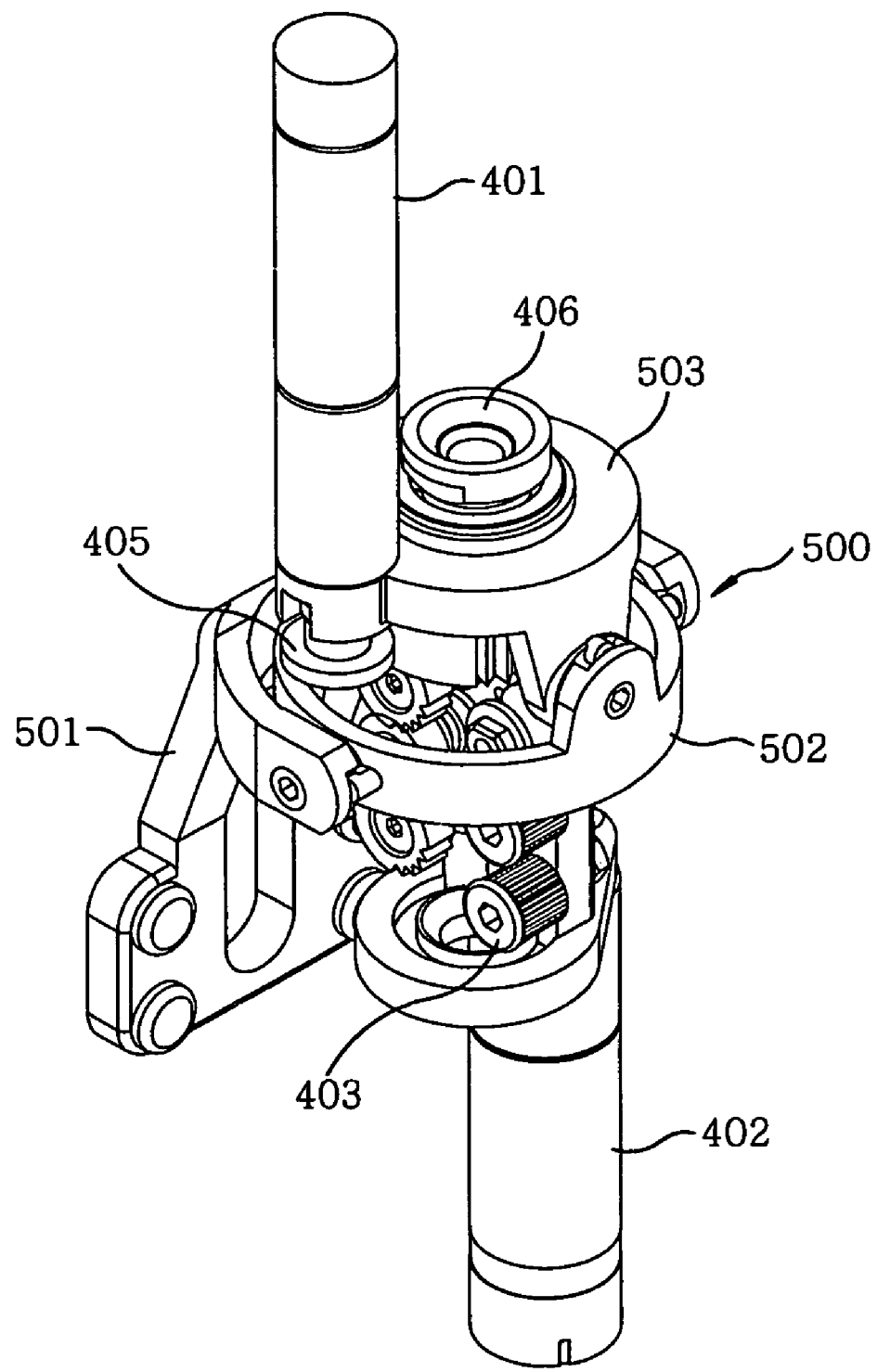
FIG. 5C is a perspective view of the pivotal mechanism which is mounted on the linear guide.

Referring to FIGS. 5A to 5B, the pivotal mechanism 500 includes a lower part 501, a middle part 502, an upper part 503. The parts 501 to 503 are pivotally coupled to each other by using bolts 502a and 503a. The lower part 501 is engaged with the carriage 300 by coupling connectors 501a to the connectors 303 of the carriage 300. The lower part 501 and the middle part 502 can be pivoted relative to each other as indicated by the arrows J2, and the upper part 503 and the middle part 502 can be pivoted relative to each other as indicated by the arrows J1. The movements J1 and J2 are orthogonal to each other. The pivotal mechanism 500 is not actively motor driven. Furthermore, the movements J1 and J2 are orthogonal to the movements S1 and S2, respectively.

Additionally, the linear guide 400 is fixed to the upper part 503 by using the fastener 406. In that case, a shaft (not shown) of the motor 401 is inserted through a hole 503d of a protruding portion 503c to be engaged with the gear 405. With such arrangements, the linear guide 400 can be pivoted relative to the carriage 300 as indicated by the arrows J1 and J2.

Referring to FIG. 6, the surgical instrument 600 includes a motor 601, an electric wire 602, a rod 603, fingers 604 and a pivot connection 605 for the end tip driving mechanism. A pair of fingers 604 is pivotally coupled to the pivot connection 605, for incising, sewing and cutting a tissue of the patient P. A wire (not shown) is connected between the fingers 604 and the motor 601 through the rod 603. The motor 601 is provided to an upper end of the surgical instrument 600 and serves to pull and release the wire. The electric wire 602 is connected to a force feedback sensor (not shown) in the surgical instrument 600. The force feedback sensor detects a feedback force applied to the fingers 604 and transmits a signal of the feedback force via the electric wire 602 to the control system. It will be appreciated that the fingers 604 can be angularly displaced about the pivot connection 605 toward and away from each other as indicated by the arrows S4.

Figure 7:
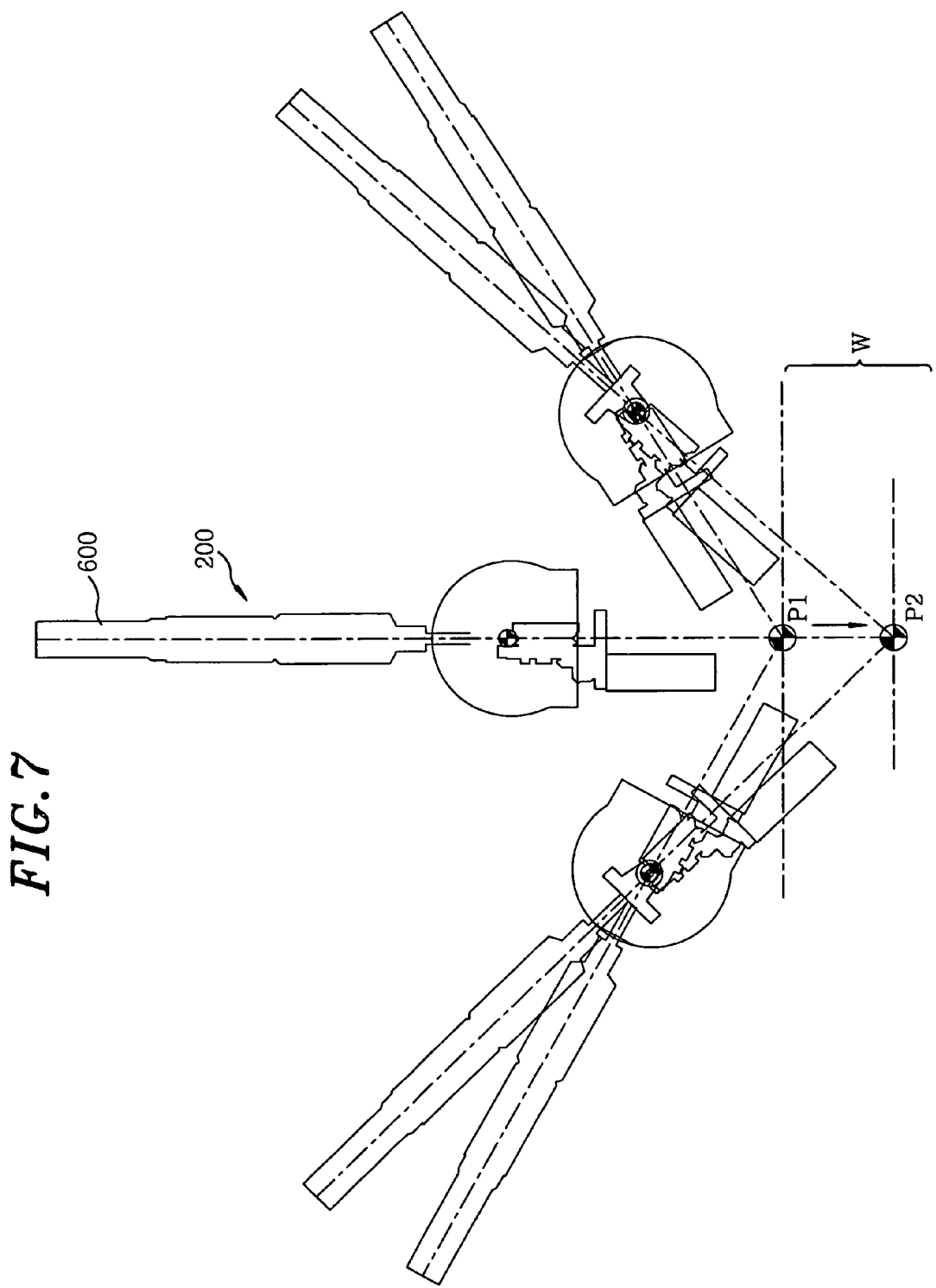
FIG. 7 is a diagram for explaining the shift of an original pivot point P1 to a new pivot point P2 with the help of the pivotal mechanism in accordance with the present invention.

With reference to FIG. 7, there will be described an operation of the pivotal mechanism 500 of the present invention. When the surgical instrument 600 inserted through an abdominal wall W of the patient P is pivoted about an original pivot point P1, normally, a port of entry on the abdominal wall W, the pivot point of the surgical instrument 600 is shifted from the original pivot point P1 to a new pivot point P2. In the present invention, by the help of the above-mentioned movements J1 and J2 of the pivotal mechanism 500, the surgical instrument 600 is pivoted to be in alignment with the pivot point P2. It will be appreciated that the shifted pivot point P2 remains stationary throughout the surgical procedure. Accordingly, tissues of the abdominal wall W surrounding the surgical instrument 600 are not excessively affected by the surgical instrument 600. Preferably, the distance between P1 and P2 is about 50 mm or less.

Figure 8A:
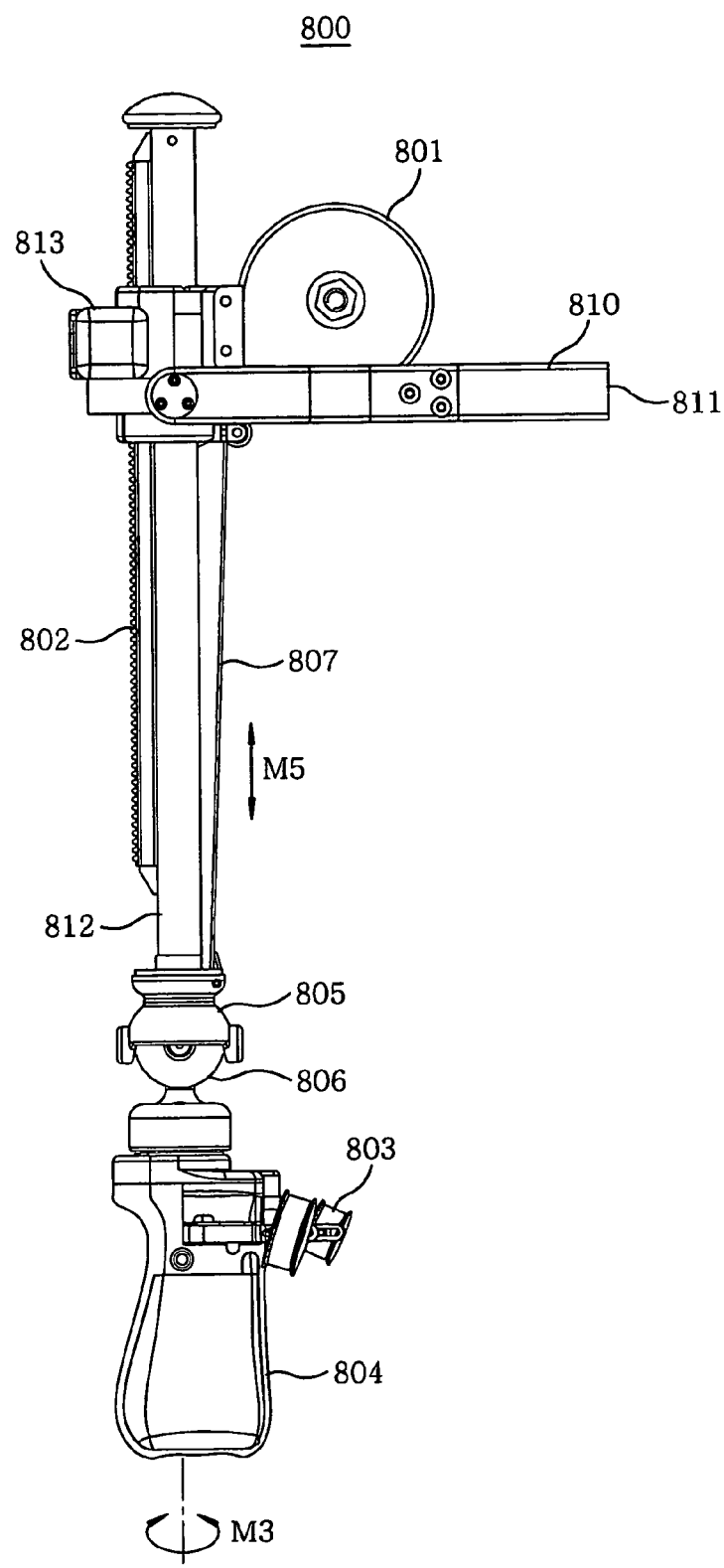
FIGS. 8A and 8B are a side view and a perspective view of a master manipulator in accordance with the present invention.
Figure 8B:
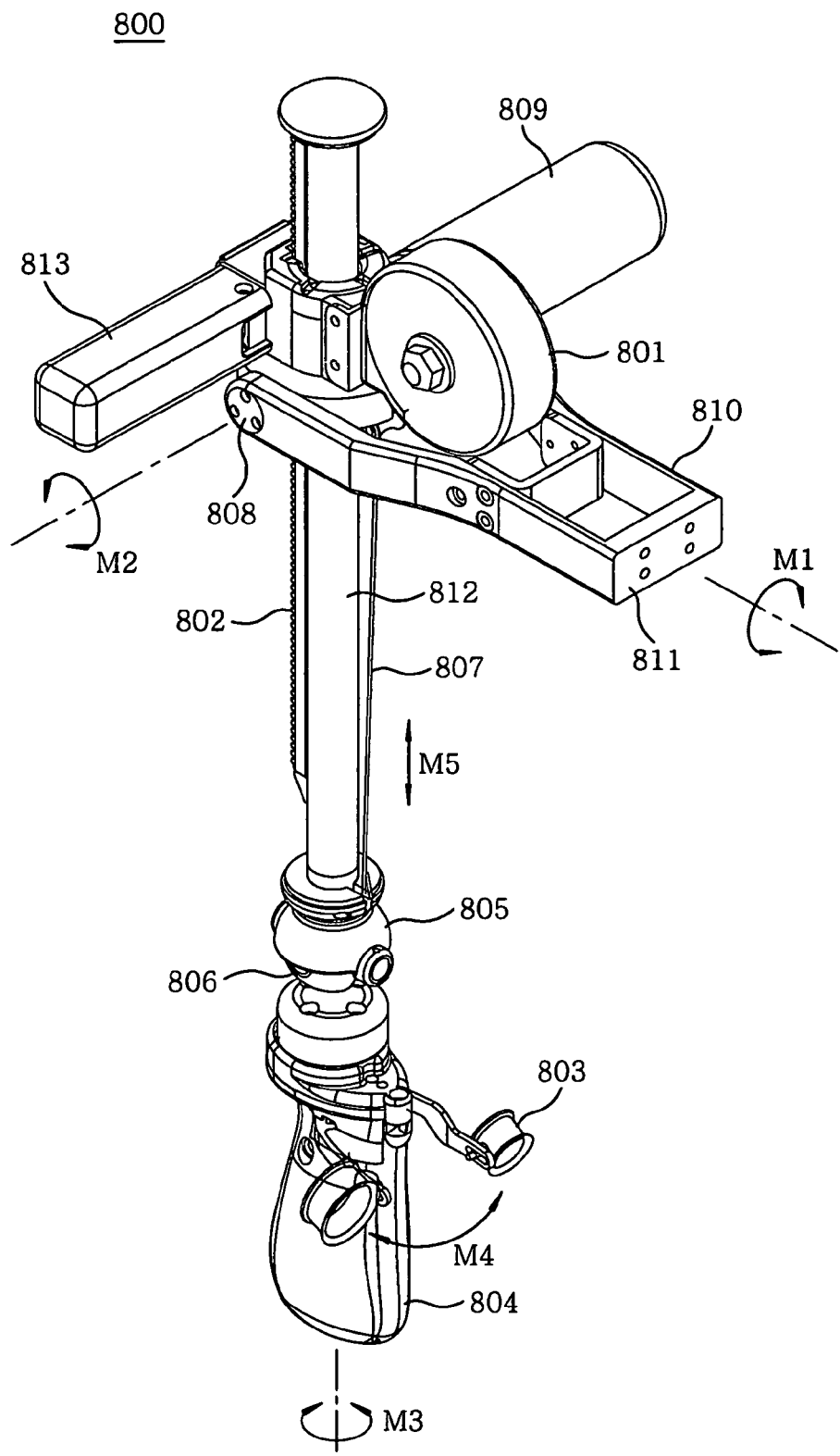

Referring now to FIGS. 8A and 8B, the master manipulator 800 includes a shaft 812; a toothed belt 802 provided to the shaft 812; a lever 810 for allowing the shaft 812 to slide as indicated by the arrows M5; pivotal connections 805, 806; a spring-biased wire wheel 801 for aiding the movement of the shaft 812 with an additional force; a wire 807 being wound up into the spring-biased wire wheel 801 as the shaft 812 moves upward, and vice versa; a handle 804 rotatably engaged with the pivotal connection 806, and being gripped by a hand of the operator O; finger seats 803 pivotally coupled to the handle 804; and a motor assembly 809 for aiding and sensing the movement of the master manipulator 800.

The lever 810 can be pivoted as indicated by the arrows M1 by connecting a first portion 811 of the lever 810 to an arm (not shown) installed in the control station 100 (see, FIG. 1). A second portion 813 of the lever 810 can be pivoted about a connection 808 with respect to the first portion 811 as indicated by the arrows M2. FIG. 1 indicates that the master manipulator 800 is installed in the control station 100. The master manipulator 800 can be displaced angularly as indicated by arrows M1 and M2.

The finger seats 803 can be angularly displaced about the handle 804 toward and away from each other as indicated by the arrows M4. And, the handle 804 can be rotated about the pivotal connection 806 as indicated by the arrows M3. The pivotal connection 806 can also be pivoted about the pivotal connection 805.

Now, the electrical connections with the master/slave movements in the control system will be described.

Each slave robotic unit 200 is operated and moved in response to movement demands from its associated master manipulator 800. Preferably, sensors (not shown, e.g., encoders, potentiometers or the like) are provided to the master manipulator 800 and the slave robotic unit 200. The control system receives input signals from the master manipulator 800, computes a corresponding movement of the surgical instrument 600 and determines positions and orientations of each slave robotic unit 200 based on the received input signals. Accordingly, the movement M1 of the master manipulator 800 is translated to the corresponding movement S1 of the slave robotic unit 200. Similarly, the movements M2 through M5 are, respectively, translated to the movements of S2 through S5.

Meanwhile, the operator O can feel feedback forces by the master manipulator 800 electrically connected with the associated slave robotic unit 200 during the operation thereof, so that the operator O can more exactly control the surgical instrument 600.

The following is a description of an operation of the surgical robotic system as described above.

A small incision is made on the patient P lying on the operation table T. Next, the semicircular rack gear guide 205 is positioned near the incision, and then, the surgical instrument 600 is allowed to pass through the incision to the surgical site. The operator O grips the handle 804 of the respective master manipulators 800 with his or her fingers fitted into the finger seats 803 to perform a surgery while monitoring the display D.

The movement M4 of the finger seats 803 is translated to the movement S4 of the fingers 604 through the control system. The motor 601 of the surgical instrument 600 is driven by an operation signal of the finger seats 803 via the control system. The wire repetitively pulls and releases the fingers 604 as the motor 601 rotates clockwise and counterclockwise. Accordingly, an incision, a sewing and a cutting operation can be performed by the fingers 607.

Meanwhile, a difficulty in controlling the surgical instrument 600, due to a mechanical load while manipulating the master manipulators 800, is minimized by using motors driven in the same directions as manipulating directions of the operator O.

In accordance with the present invention, the surgical robotic system can reduce recovery time of a patient by performing a surgery in a minimal invasive manner. Further, by shifting a pivot point of a surgical instrument on the fat layer or the abdominal wall of the patient P during the surgery, it is possible to reduce repelling forces of the abdominal wall against the surgical instrument.

While the invention has been shown and described with respect to the preferred embodiments, it will be understood by those skilled in the art that various changes and modification may be made without departing from the scope of the invention as defined in the following claims.

What is claimed is:

1. A robotic surgical system for performing a surgical procedure on a patient, comprising:
   a master manipulator installed at a control station to be manipulated by an operator;
   a plurality of slave robotic units for conducting the surgical procedure;
   a control system for electrically associating the master manipulator with the slave robotic units to allow each of the slave robotic units to be remotely controlled by the associated master manipulator; and
   a display for viewing the surgical procedure,
   wherein said each of the slave robotic units includes:
   a forearm uniquely provided to said each of the slave robotic units;
   a surgical instrument for being inserted to a surgical site of the patient, the surgical instrument being held by the forearm and including a rod and an end tip tool pivotably connected to one end of the rod;
   a yaw driving mechanism for moving the rod of the surgical instrument in a yaw direction, the yaw driving mechanism including a wrist coupled to the forearm and rotationally driven in the yaw direction;

a pitch driving mechanism for moving the rod of the surgical instrument in a pitch direction, the pitch driving mechanism including a semicircular rack gear guide supported by the wrist and further including a carriage movably mounted on the semicircular rack gear guide;

a linear driving mechanism for linearly moving the rod of the surgical instrument, the linear driving mechanism being disposed on the carriage;

a rotational driving mechanism for rotating the rod of the surgical instrument about a longitudinal axis of the rod, the rotational driving mechanism being disposed on the carriage; and a pivotal mechanism for allowing the rod of the surgical instrument to be freely pivoted, the pivotal mechanism being disposed on the carriage.

2. The robotic surgical system of claim 1, wherein the yaw driving mechanism further includes:
   a motor installed in the forearm; and
   a shaft rotated by the motor and coupled to the wrist.

3. The robotic surgical system of claim 2, wherein the pitch driving mechanism further includes:
   a motor, a pinion gear and guide rollers provided in the carriage, wherein the pinion gear is driven by the motor of the pitch driving mechanism,
   wherein the semicircular rack gear guide is provided between the pinion gear and the guide rollers so that the carriage is moved along the semicircular rack gear guide in the pitch direction.

4. The robotic surgical system of claim 3, wherein the pivotal mechanism includes:
   a first part engaged with the carriage of the pitch driving mechanism;
   a second part pivotally connected to the first part; and
   a third part pivotally connected to the second part, the third part being fixed to the linear driving mechanism.

5. The robotic surgical system of claim 4, wherein the pivot movements of the second part and the third part are orthogonal to each other.

6. The robotic surgical system of claim 4, wherein the linear driving mechanism includes:
   a linear guide fixed to the third part of the pivotal mechanism; and
   a motor and rollers provided in the linear guide, wherein the rollers are driven by the motor of the linear driving mechanism, wherein the rod of the surgical instrument is inserted between the rollers so as to be linearly moved by the rollers,
   wherein the linear guide is pivotably mounted on the carriage of the pitch driving mechanism through the pivotal mechanism such that the linear guide is allowed to be pivoted relative to the carriage of the pitch driving mechanism.

7. The robotic surgical system of claim 4, wherein the rotational mechanism includes:
   a motor coupled to the first part of the pivotal mechanism;
   a first gear driven by the motor; and
   a second gear inserted by the rod, the second gear being driven by the first gear.

8. The robotic surgical system of claim 1, wherein the pitch driving mechanism further includes:
   a motor, a pinion gear and guide rollers provided in the carriage, wherein the pinion gear is driven by the motor, and
   wherein the semicircular rack gear guide is provided between the pinion gear and the guide rollers so that the carriage is moved along the semicircular rack gear guide in the pitch direction.

9. The robotic surgical system of claim 1, wherein the linear driving mechanism includes:
   a linear guide; and
   a motor and rollers provided in the linear guide, wherein the rollers are driven by the motor, wherein the rod of the surgical instrument is inserted between the rollers so as to be linearly moved by the rollers, and
   wherein the linear guide is pivotally connected to the pitch driving mechanism through the pivotal mechanism.

10. The robotic surgical system of claim 1, wherein the pivotal mechanism includes:
    a lower part engaged with the pitch driving mechanism;
    a middle part pivotally connected to the lower part; and
    an upper part pivotably connected to the middle part, the upper part being fixed to the linear driving mechanism.

11. The robotic surgical system of claim 10, wherein the pivot movements of the middle part and the upper part are orthogonal to each other.

12. The robotic surgical system of claim 1, wherein the end tip tool includes a pair of fingers, and
    wherein the surgical instrument further includes an end tip driving mechanism for driving the fingers and thereby incising, sewing, or cutting the surgical site.

13. The robotic surgical system of claim 12, wherein the end tip driving mechanism includes a motor and a wire which is connected between the fingers and the motor of the end tip driving mechanism.

14. The robotic surgical system of claim 1, wherein the rotational mechanism includes:
    a motor coupled to the pivotal mechanism;
    a first gear driven by the motor; and
    a second gear inserted to the rod, the second gear being driven by the first gear.

15. The robotic surgical system of claim 1,
    wherein the linear driving mechanism, the rotational driving mechanism and the pivotal mechanism are coupled to each other.

16. The robotic surgical system of claim 1, wherein the yaw driving mechanism, the pitch driving mechanism, the linear driving mechanism, and the pivotal mechanism serve to move the rod of the surgical instrument to the surgical site.

17. The robotic surgical system of claim 1, wherein the pivotal mechanism is configured to shift a pivot point of the rod of the surgical instrument depending on a relative position with respect to the surgical site so that affection of the rod of the surgical instrument on the surgical site is restrained.

18. The robotic surgical system of claim 17, wherein the distance between an original pivot point of the rod of the surgical instrument and the shifted pivot point of the rod of the surgical instrument is equal to or less than 50 mm.

19. The robotic surgical system of claim 1, wherein the pivotal mechanism serves to allow the rod of the surgical instrument to be pivoted without the help of an electrical power source.

20. The robotic surgical system of claim 1, further comprising:
    an operation table on which the patient is placed,
    wherein the forearm of said each of the slave robotic units is mounted on the operation table via a holder.

* * * * *